United States Patent
Stevens

(10) Patent No.: US 11,851,579 B2
(45) Date of Patent: Dec. 26, 2023

(54) PAINT AND OTHER MATERIALS INCLUDING A TAGGANT

(71) Applicant: Henry Guy Stevens, Cheltenham (GB)

(72) Inventor: Henry Guy Stevens, Cheltenham (GB)

(73) Assignee: Henry Guy Stevens, Cheltenham (GB)

( * ) Notice: Subject to any disclaimer, the term of this patent is extended or adjusted under 35 U.S.C. 154(b) by 337 days.

(21) Appl. No.: 17/296,100

(22) PCT Filed: Dec. 30, 2019

(86) PCT No.: PCT/GB2019/053705
§ 371 (c)(1),
(2) Date: May 21, 2021

(87) PCT Pub. No.: WO2020/136381
PCT Pub. Date: Jul. 2, 2020

(65) Prior Publication Data
US 2022/0010145 A1    Jan. 13, 2022

(30) Foreign Application Priority Data
Dec. 28, 2018   (GB) ..................... 1821277

(51) Int. Cl.
*C09D 5/22* (2006.01)
*C09D 7/61* (2018.01)
(Continued)

(52) U.S. Cl.
CPC ................. *C09D 5/22* (2013.01); *C09D 5/14* (2013.01); *C09D 5/18* (2013.01); *C09D 7/61* (2018.01);
(Continued)

(58) Field of Classification Search
CPC ... C09D 5/22; C09D 7/61; C09D 5/14; C09D 5/18; C09K 11/7774; G01B 11/0616;
(Continued)

(56) References Cited

U.S. PATENT DOCUMENTS

| 4,567,370 A | 1/1986 | Falls |
| 2008/0024771 A1 | 1/2008 | Crawford et al. |

(Continued)

FOREIGN PATENT DOCUMENTS

| CN | 101880487 A | 11/2010 |
| DE | 102017004496 A1 | 11/2018 |

(Continued)

OTHER PUBLICATIONS

Further Search Report for Patent Application GB1821277.9 dated Mar. 18, 2022; 2 pp.
(Continued)

*Primary Examiner* — David P Porta
*Assistant Examiner* — Fani Polyzos Boosalis
(74) *Attorney, Agent, or Firm* — Armstrong Teasdale LLP

(57) ABSTRACT

There is provided a paint including a pigment, a carrier liquid, a binder, one or more additives, and a taggant corresponding to the one or more additives. The taggant is provided in an amount up to substantially 0.1% by weight of the paint. The taggant is excitable by infra-red or UV light at one wavelength to emit light at one or more other wavelengths, the emission wavelength or spectrum of the taggant being indicative of the additive(s) in the paint. A method of authenticating the paint on a substrate is also provided.

20 Claims, 1 Drawing Sheet

(51) Int. Cl.
*C09D 5/14* (2006.01)
*C09D 5/18* (2006.01)
*G01B 11/06* (2006.01)
*G01N 21/64* (2006.01)
*G01N 21/84* (2006.01)
*G01N 33/32* (2006.01)
*C09K 11/77* (2006.01)

(52) U.S. Cl.
CPC ...... *C09K 11/7774* (2013.01); *G01B 11/0616* (2013.01); *G01N 21/6428* (2013.01); *G01N 21/8422* (2013.01); *G01N 33/32* (2013.01); *G01N 2021/6439* (2013.01); *G01N 2021/8427* (2013.01)

(58) Field of Classification Search
CPC .......... G01N 21/6428; G01N 21/8422; G01N 33/32; G01N 2021/6439; G01N 2021/8427
See application file for complete search history.

(56) References Cited

U.S. PATENT DOCUMENTS

| | | |
|---|---|---|
| 2008/0087189 A1 | 4/2008 | Lin et al. |
| 2008/0290649 A1 | 11/2008 | Klein et al. |
| 2009/0286250 A1 | 11/2009 | Hayward |
| 2010/0056688 A1* | 3/2010 | Greer ............ C08K 3/22 524/413 |
| 2013/0015369 A1 | 1/2013 | Rapoport et al. |
| 2015/0252255 A1 | 9/2015 | Wang et al. |
| 2016/0202606 A1 | 7/2016 | Prasad et al. |
| 2017/0233577 A1 | 8/2017 | Henary et al. |
| 2018/0307128 A1 | 10/2018 | Joseph et al. |

FOREIGN PATENT DOCUMENTS

| | | |
|---|---|---|
| JP | S62167372 A | 7/1987 |
| JP | 2001040343 A | 2/2001 |
| JP | 2011507982 A | 3/2011 |
| WO | 0250570 A2 | 6/2002 |
| WO | 2004089640 A2 | 10/2004 |
| WO | 2009136921 A1 | 11/2009 |
| WO | 2012172018 A1 | 12/2012 |

OTHER PUBLICATIONS

International Search Report and Written Opinion for Application PCT/GB2019/053705; dated Jun. 18, 2020; 18 pp.
International Preliminary Report on Patentability for Application PCT/GB2019/053705 dated May 14, 2021; 17 pp.
"Automatic Sorting of Recyclable Materials with NIR Technology", WasteMINZ 19th Annual Conference & Expo, Nov. 6-8, 2007; Hamilton, New Zealand; URL: https://silo.tips/download/unisort-nir-technologies; retrieved May 14, 2021; 5 pp.
Combined Search and Examination Report for Application GB1821277.9 dated Jun. 27, 2019; 7 pp.
Written Opinion of the International Preliminary Examining Authority for Application PCT/GB2019/053705 dated Feb. 19, 2021; 4 pp.
Written Opinion of the International Preliminary Examining Authority for Application PCT/GB2019/053705 dated Nov. 25, 2020; 10 pp.
European Search Report for EP 22186454 dated Aug. 12, 2022; 4 pps.
JP Office Action for JP2021534328 dated Sep. 27, 2023; 5 pps.

* cited by examiner

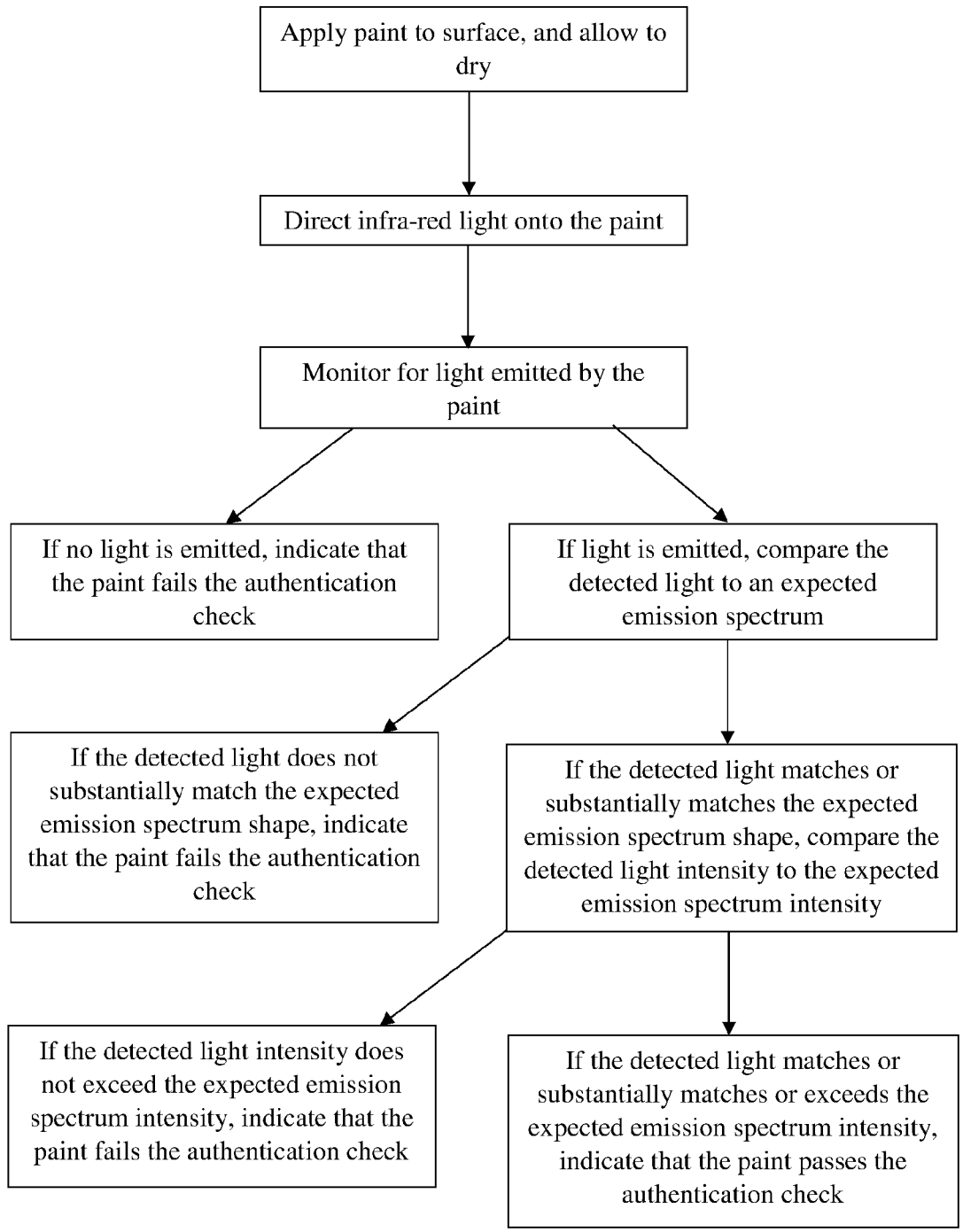

PAINT AND OTHER MATERIALS INCLUDING A TAGGANT

CROSS-REFERENCE TO RELATED APPLICATIONS

This application is a U.S. National Phase Application of PCT/GB2019/053705, filed Dec. 30, 2019, which claims the benefit of priority to GB Application No. 1821277.9, filed Dec. 28, 2018, the contents of which are hereby expressly incorporated by reference in their entirety.

FIELD OF THE INVENTION

The present invention relates to a paint or varnish including a taggant which is indicative of additives in the paint; a method of non-destructively authenticating the identity of a paint or varnish comprising a taggant; a taggant composition for addition to a paint or varnish, and a method of doing so; a plastic, composite material or building element including a taggant; and a method of sorting a mixture of items for recycling using a taggant.

BACKGROUND TO THE INVENTION

Specialist paints or coatings have been developed to be decorative but also to have functional properties suitable for various applications. Examples of such paints include compositions or formulations specifically designed to resist fire damage or inhibit fire propagation, or to inhibit bacterial growth, or to resist staining or weathering, to name a few. For example, fire-resistant paints are preferred along corridors and stairwells for fire escape routes.

The task of painting is generally contracted out to a handyman or small team of painters who obtain and apply the paint. Specialist paints or coating materials tend to be relatively expensive per unit weight, compared to non-specialist paints like low-cost emulsions used to decorate rooms at home, for example. Thus, in some instances, the required paint with fire-resistant (or other) properties is not used, and a cheaper paint that looks the same is applied. This can be dangerous, if for example antibacterial paint is not used in a food processing area, or potentially catastrophic if for example a non-fire-resistant paint is used in a residential block.

In some cases, because multiple layers (primer, undercoat, top coat) need to be applied to provide sufficient fire resistance, for example, a specialist paint may be mixed with a cheaper paint to make it go further, or only the surface layer of paint may include the specialist paint, for example.

In the case of a genuine error, the wrong type of specialist paint may be used. It is also sometimes the case that the importance of using a specific paint is lost during the contracting and sub-contracting process, so that the person actually doing the painting only believes a particular colour is needed, for example.

It is not possible to determine on-site whether the correct paint has been used. Instead, it would require taking samples and testing them, which would damage the protective layer provided by the paint or coating. It is also not possible to determine if the paint has been applied to the required thickness, that is to say that a sufficient number of paint layers have been applied, since monitoring the contractors is typically impractical.

More generally, there is a problem with easily checking or confirming that the correct building elements have been used to build or retro-fit a building. For example, the cladding fitted to the outside of the Grenfell Tower building in London did not meet the required fire safety standards, but this was only identified following a disastrous fire in that building in 2017 where many lives were lost. There was no easily identifiable difference between two different grades of cladding—one which had limited fire resistance, and one which had relatively better fire resistance—and so no easy way of identifying what kind of cladding was on the exterior of the building. Performing such checks after cladding is installed is slow and presents a risk because it requires working at height, and perhaps retrieval and destructive testing of a sample.

Many modern building elements tend to include plastic or composite materials, and it can be difficult to identify the exact material used. It is therefore difficult to know whether the building element being used meets the required safety standards. On a related note, this also makes it difficult to recycle building materials easily, because it is difficult or impossible to easily identify the type of plastic or composite material used.

In a more general sense, plastics can be labelled with a recycling label (in the UK, typically provided as a numeral within a triangle formed of 3 arrows on plastic packaging) to indicate recyclability. However, this still requires the symbol to be manually found, read by the consumer, and the item provided in the correct recycling bin. This requires effort and knowledge on the part of the consumer. Inevitably, mistakes are made in the manual sorting process, and these are difficult to identify and rectify later in the recycling process. Batches of recyclable plastic can therefore become contaminated and may, once put through a recycling process, result in a batch of recycled plastic which is unfit for purpose, leading to more waste. There is no easy way to automatically sort multiple different varieties of plastic for recycling.

It is an object of the present invention to reduce or substantially obviate the aforementioned problems.

STATEMENT OF INVENTION

According to a first aspect of the present invention, there is provided a paint comprising a pigment, a carrier liquid, a binder, one or more additives, and one or more taggants corresponding to the one or more additives, in which the taggant is provided in an amount up to substantially 0.1% by weight of the paint, and in which the taggant is excitable by infra-red (IR) or ultraviolet (UV) light at one wavelength to emit light at one or more other wavelengths, the emission wavelength or spectrum of the taggant being indicative of the additive(s) in the paint.

Optional features are presented in dependent claims 2 to 12.

This provides a paint which can be evaluated once dry, so that there is a means of non-destructively checking whether the paint has required attributes. The taggant may be considered to be a security marker or compound. Its presence provides the ability to test the paint because it is responsive to specific wavelengths of light. The presence of the taggant therefore substantially mitigates the risk that a particular area, such as a fire escape route or food preparation area, will be incorrectly signed off as fit for purpose, because the paint can be evaluated without destructive testing. This makes any errors traceable and the person or body responsible for such errors can be held accountable, whether the wrong paint (or insufficient paint) was used accidentally or on purpose. The paint may be provided as a coating, on an object or surface like a wall, for example.

The taggant may include a plurality of inorganic or ceramic taggants. The taggant may luminesce when the correct wavelength of light is directed onto it.

The plurality of taggants may be provided in a signature ratio. The use of a particular ratio of taggants provides a signature or fingerprint emission spectrum for use in authenticating the identity of the paint. That is, to ensure that the correct paint has been used. The signature emission spectrum is difficult to forge because the relative proportions of each taggant affect the relative intensities of the peaks in the spectrum. Thus, a paint without additives conferring fire-resistance (or other properties, as discussed above) cannot realistically be modified before or after painting to pass authentication.

The plurality of taggants may include a plurality of lanthanide elements to provide the signature emission spectrum. However, any suitable commercially available taggant may be used. The taggant may be selected to include one or more of the following: $Y_2O_3:Eu^{3+}$; $CeMgAl_{11}O_{19}:Tb^{3+}$; $BaMgAl_{10}O_{17}:Eu$; $La_{0.60}Ce_{0.27}Tb_{0.13}PO_4$; $GdMgB_5O_{10}:Ce,Tb$; $(Sr,Ba,Ca)_5(PO_4)_3Cl:Eu^{2+}$. These are just examples of many potentially suitable taggants.

The taggant may be excitable using UV light. The taggant may be excitable using IR light at a wavelength of around 840 nm. However, the wavelength used for excitation will be selected according to the taggant. Different lanthanides absorb strongly at different wavelengths, and so it may be preferable to use multiple excitation wavelengths.

By using multiple lanthanide elements, a complex emission spectrum is produced when the taggants are excited, which is again difficult to forge. A combination or blend of taggant compounds may be used. For example, a custom combination of $CeMgAl_{11}O_{19}:Tb^{3+}$, $BaMgAl_{10}O_{17}:Eu$ and $La_{0.60}Ce_{0.27}Tb_{0.13}PO_4$ may be used. The ratio of the components affects the spectrum and is selected to be specific to a particular paint or subset of paints.

The taggant preferably does not absorb or become excited by visible light. Incident visible light should only be reflected. So, the taggant should not fluoresce or phosphoresce on exposure to indoor lighting, and preferably not in sunlight. The taggant should not affect the apparent colour of the paint when dry, to avoid an adverse impact on existing colour systems of paint manufacturers.

The taggant may comprise between 0.005% and 0.05% by weight of the paint. The taggant may comprise between 0.01% and 0.025% by weight of the paint. In other words, per unit weight of paint, the percentage of taggant is a fractional amount of the overall paint. The expected intensity of the emission spectrum is affected by the proportion of taggant, so using a very small amount again makes it difficult to correctly forge the paint. Controlling the proportion of taggant is also useful to avoid adversely impacting the other properties (e.g. rheology or viscosity) of the paint, and because the taggant is relatively expensive it is preferable to limit the amount used.

The taggant may be evenly dispersed and suspended in the carrier liquid. This means that, when applied to a wall for example, it does not matter what section is tested during authentication because the emission response should be substantially uniform across the wall (assuming no impurities and even thickness of paint).

The low loading of the taggant can present a challenge when it comes to evenly dispersing the taggant within the paint. A dispersant may be used to aid taggant dispersion. The dispersant may be a conventional dispersant like the one used to aid dispersion of the pigment or additives, for example.

The taggant may have a particle size or particle size range suitable for remaining in suspension to ensure homogenous distribution. The particle size or range should be no larger than the particle size or range of the other paint constituents, to ensure that the rheology and surface finish of the paint is substantially unaffected by the presence of the taggant. It also avoids the need to make further adaptations to keep the taggant in suspension. For example, the particle size range may be 0.9 to 3.3 microns.

The additive(s) may include one or more fire-resistant and/or fire-responsive components or compounds. For example, aluminium hydroxide $(Al(OH)_3)$ may be included for its flame retardation properties. The taggant may emit red or reddish light (around 620 nm for example) following infra-red or UV excitation for indicating that fire-resistant and/or fire-responsive components are present. The paint or additives may comprise an intumescent component.

The additive(s) may include one or more antibacterial components or compounds. For example, silver ions may be included. The taggant may emit green or greenish light (e.g. around 530-550 nm) following infra-red or UV excitation for indicating that antibacterial compounds are present.

The additive(s) may include one or more antiviral components or compounds.

The additive(s) may include one or more antifungal components or compounds.

The additive(s) may include one or more non-slip or anti-slip components or compounds. This is useful where the paint may be applied on a walkway.

The additives may include one or more surfactants or thickeners, for example.

The taggant may decompose on exposure to fire, but should only release non-toxic gases, or not release an amount of a toxic gas which would be cause irreparable harm to a human being. Preferably the taggant is environmentally friendly. The taggant should not react with the other constituents of the paint. The taggant may leave a residue after a fire which allows an investigator to ascertain whether the required paint was used. In other words, the taggant can serve as a marker both before and after a fire, for validating whether the correct paint has been applied. This particularly applies where a ceramic taggant is used.

At least the pigment and the additives may be transparent (or substantially translucent) to at least some of the wavelengths at which the taggant absorbs and emits light. This is to avoid overly attenuating light emissions from paint layers which are located below the surface of the paint, since the light emissions from these layers are an indication of the thickness of the paint. For example, the thickness of fire-resistant paint maybe be around 100-200 microns (μm). The increased emission intensity from the paint layers below the surface needs to be reliably measurable, so at least part of the emission spectrum of the taggant needs to make it through the layers for detection.

The taggant may include an up-converting phosphor or component (an upconverter) which, in use, absorbs light (e.g. IR light) and subsequently emits light at a shorter wavelength than that of the absorbed light. The taggant may include a down-converting phosphor or component (a downconverter) which, in use, absorbs light (e.g. UV light) and subsequently emits light at a longer wavelength than that of the absorbed light. The taggant may include both components, that is to say both an upconverter and a downconverter, to provide an emission spectrum which is more secure. There may be a time delay between initial excitation and subsequent emission where the emission occurs via phosphorescence.

There may be provided a container, such as a can or tin, which comprises paint according to the first aspect of the invention.

According to a second aspect of the present invention, there is provided a method of non-destructively authenticating the identity of a paint or varnish on a substrate, optionally a non-metal substrate, comprising the steps of:

a) directing light onto the paint or varnish for exciting a taggant if present in the paint or varnish (that is, a taggant expected to be in the paint or varnish);

b) detecting light, if any, which is subsequently emitted from the paint or varnish; and c) comparing the detected light to an expected signature emission wavelength or spectrum of the paint or varnish, to determine whether the correct paint varnish has been applied and whether it has been applied to the substrate correctly/properly.

Optional features are presented in dependent claims 15 to 25. The paint may be paint according to the first aspect of the invention.

This provides a way to establish (i) whether the correct paint or varnish has been applied, and (ii) whether that paint has been applied sufficiently thickly to meet the required specification. The advantages are similar to the first aspect of the invention. The test can be carried out quickly and easily on-site, allowing sign-off at the same time if the paint passes authentication. If a taggant is not detected then the paint fails authentication. The method may be used (optionally repeatedly) as part of a quality check or control process for a building. This may include an inspection for initial sign-off following construction, or an annual inspection, for example.

Step (c) may include comparing the intensity of the detected light to an expected intensity value or range for assessing the thickness of the paint on the substrate. Thicker paint will usually give a relatively more intense reading. This can be compared to a known calibration curve to establish the thickness of the paint non-invasively. If the intensity reading is too low, the paint is not thick enough and the paint fails authentication. If the paint is thick enough, known due to taggant response on irradiation, then the paint passes authentication.

The use of a taggant makes it possible to measure paint thickness on non-metal substrates, which would not normally reflect incident IR or other light and allow reliable determination of paint layer thickness. However, it is possible to measure paint thickness in this way on a metal substrate too.

The authentication process may be performed once the paint is dry. It may take up to a week for the paint to fully dry or cure. It is preferable to wait until the paint is fully dry or cured to ensure that the readings which are taken correlate accurately with the calibration curve being used.

Steps (a) to (c) may be performed using a hand-held device or reader. The device may be held against or near the paint on the substrate. The device may include an IR emitter, such as an IR laser or IR LEDs, which may be high intensity for causing emission from a taggant. Example excitation wavelengths depend on the taggant used, but the laser or LEDs may emit at 940 nm or 980 nm for example. Alternatively, a UV emitter may be provided.

The hand-held device may include a sensor capable of detecting visible light, infra-red light, or both visible and infra-red light. In some cases, the sensor may be capable of detecting UV light, preferably near-ultraviolet. The hand-held device may be programmed with a plurality of signature emission spectra, for authenticating a plurality of different paints. The reader may be able to identify the colour and/or determine light intensity.

The reader may include an enclosure positionable against the paint, to keep the light (e.g. laser) from the emitter contained and avoid the need for eye protection when using the reader.

An image may be recorded of the paint (or each section of paint) during or immediately following excitation, for authenticating the or each painted area off-site. A timestamp may be applied to or associated with the recorded image. Location data, such as a GPS position stamp, may be applied to or associated with the recorded image. This is useful where there are a large number of painted areas to authenticate and there is insufficient time to do so whilst access to the painted areas is available. It also allows evidence to be obtained and kept for the future, in case there is ever a question about the paint that was used. For example, in the event of a fire and attribution of liability for harm caused to a person, being able to show that the paint met the specification for fire resistance will potentially mitigate sanctions. A camera may be used to record the image, so that the relevant emission spectrum can be recorded.

According to a third aspect of the present invention, there is provided a varnish comprising a fluid, one or more additives, and a taggant corresponding to the one or more additives, in which the taggant is provided in an amount up to substantially 0.1% by weight of the varnish, and in which the taggant is excitable by infra-red or ultraviolet light at one wavelength to emit light at one or more other wavelengths, the emission wavelength or spectrum of the taggant being indicative of the additive(s) in the varnish.

The fluid may comprise components found in conventional varnishes, e.g. independently selected from any combination of the following: drying oil, resin, solvent. In some cases, a pigment may be provided.

The varnish may include any feature or combination of features presented with respect to the first aspect of the invention.

According to a fourth aspect of the present invention, there is provided a taggant composition for addition to a paint or varnish, the taggant composition comprising a taggant, one or more additives, and a dispersant, the taggant corresponding to the one or more additives, in which the taggant is excitable by infra-red or ultraviolet light at one wavelength to emit light at one or more other wavelengths, the emission wavelength or spectrum of the taggant being indicative of the additive(s) in the taggant composition.

Optional features are presented in the dependent claims.

The taggant composition may be added to an existing paint or varnish on site. This can be done immediately prior to application of the paint or varnish or a wall, for example. This simplifies manufacture by keeping existing paint or varnish manufacturing processes the same, followed by adding/mixing the taggant composition into the paint at the point of use. It also results in more efficient transport of bulk quantities of containers of the taggant composition.

Of course, the paint or varnish must still be fit for purpose, and suitable checks may be carried out to verify the paint or varnish before a taggant composition is provided for incorporation into that paint or varnish.

According to a fifth aspect of the present invention, there is provided a method of manufacturing or modifying a paint or varnish, the method including the steps of:

a) providing a paint comprising a pigment, a carrier liquid, and a binder; or providing a varnish;

b) providing a taggant composition according to the fourth aspect of the invention, in which the taggant in the taggant composition is provided in an amount up to substantially 0.1% by weight of the paint or varnish; and c) mixing the taggant or taggant composition into the paint or varnish.

This can provide a paint or varnish according to the first or third aspects of the invention. The mixing step may occur on or at the site where the paint or varnish is to be applied.

The paint, varnish and/or taggant composition may include any feature or features presented in any other aspect of the invention.

The paint or varnish may be provided in a container. The container may be lidded. The container may be small enough to carry by hand, although it may be poured or emptied into a larger vessel for mixing (step (c)).

The taggant composition may be provided in a smaller container for addition to the paint/varnish container, or the vessel paint or varnish is poured into.

According to a sixth aspect of the present invention, there is provided a plastic or composite material comprising a body and a taggant distributed within the body, in which the taggant is provided in an amount up to substantially 0.1% by weight of the plastic or composite material, and in which the taggant is excitable by infra-red or ultraviolet light at one wavelength to emit light at one or more other wavelengths, the emission wavelength or spectrum of the taggant being indicative of the type of plastic or composite material forming the body.

This provides a useful way to identify and sort plastic or composite materials for recycling. The taggant may be included in an extruded plastic body or fibres, for example.

Optional features are presented in the dependent claims.

The taggant may be provided in a masterbatch of the plastic or composite material. The taggant may be distributed throughout the material, allowing for fragments of material to be easily traced, such as in the event of a hit-and-run road traffic incident, for example.

The plastic or composite material may include any feature or features of the taggant presented in any other aspects of the invention.

According to a seventh aspect of the invention, there is provided a building element selected from a group comprising: flooring, such as a carpet, a floor tile, or a linoleum; and cladding for an exterior of a building; in which the building element comprises a body and taggant distributed through the body, in which the taggant is provided in an amount up to substantially 0.1% by weight of the building element, and in which the taggant is excitable by infra-red or ultraviolet light at one wavelength to emit light at one or more other wavelengths, the emission wavelength or spectrum of the taggant being indicative of the identity of the building element.

This allows for inspection of the properties of the flooring or cladding, to ensure that the required type has been used and not substituted for a cheaper, inferior product which does not meet the required safety standards.

The check can be performed in a similar way to the method of the second aspect of the invention. For example, to non-destructively authenticate the identity of a building element:

a) direct light onto the building element to excite a taggant (if present);

b) detect light, if any, which is subsequently emitted from the building element; and c) compare the detected light to an expected signature emission wavelength or spectrum corresponding to the expected building element, to determine whether the building element has the expected identity and properties.

Optional features are presented in the dependent claims.

The building element may include any feature or features of the taggant presented in any other aspects of the invention.

According to an eighth aspect of the invention, there is provide a method of sorting a mixture of items of different materials for recycling, using an automated system, the method comprising the steps of:

a) directing light onto one of the items for exciting a taggant, if present;

b) detecting light, if any, which is subsequently emitted from that item;

c) comparing the detected light to a record or database of signature emission wavelengths or spectra for taggants;

d) repeating steps (a) to (c) for at least one more of the remaining items, or preferably some or all of the remaining items; and e) based on the results of steps (a) to (d), automatically sorting the mixture of items into at least one set of items of the same or substantially similar material for recycling as a batch or part of a batch.

This allows for easier, automatic (or semi-automated) sorting of mixed materials (particularly plastics) for recycling. It avoids contamination by human error in sorting plastics, both by type and by whether a plastic is in fact recyclable. For example, the huge variety of different plastics used in packaging can therefore be subdivided into groups of items which can be recycled together to recover a useable recycled product/material.

It may also be used to identify and sort out materials which are themselves made of recycled material, but that material is not suitable for recycling.

Optional features are presented in the dependent claims.

Different plastics should include different taggants in order to allow efficient sorting. The taggants may remain in situ during the recycling process, so grouped items should have similar or the same taggants (or ratios).

If taggant is lost or reduced during the recycling process, then this can be an indicator for the material having been recycled x number of times if subsequently sorted by the same process.

The mixture may include a plurality of plastic items made of different plastics.

An existing recycling system or plant may be fitted with a suitable light emitting system, one or more light emission detector, a sorting mechanism and an electronic controller programmed to control the sorting mechanism according to the detector results in order to carry out the above method.

The taggant in this aspect of the invention may include any feature or features presented with respect to any of the other aspects of the invention.

In any aspect of the invention, a taggant may: absorb infra-red light and emit UV light or emit visible light; or absorb UV light and emit visible light or IR light.

In any aspect of the invention, the emission (such as UV emission) from the taggant(s) may be used to assess the thickness of the paint or material containing the taggant. The emission or colour of the product may be used to identify the product or to identify the product supplier, and/or the date of manufacture of the product. That is, the taggant(s) may be selected to provide a means of authenticating the product as well as a means of checking the origin and/or age of the product. This is very useful for products such as paint which cannot carry a conventional barcode on the product itself.

BRIEF DESCRIPTION OF THE DRAWINGS

For a better understanding of the present invention, and to show more clearly how it may be carried into effect, reference will now be made by way of example only to the accompanying drawings, in which:

FIG. 1 shows a flowchart of a process for authenticating the identity of a paint.

DESCRIPTION OF PREFERRED EMBODIMENTS

Paint includes a pigment or series of pigments to provide a desirable colour. Paint also includes a binder which enables the paint to properly adhere to a substrate or surface. Paint further includes a carrier fluid or solvent, which allows the other components to distributed homogenously, and enables application of the paint to the substrate or surface. The carrier fluid or solvent is selected to evaporate after application of the paint, so that the paint dries or sets on the substrate. Conventional versions of these components (pigment(s), binder, carrier) are used in this embodiment.

Additives are included in the paint according to the desired usage. For example, outdoor paint will include weather-resistant additives. Paint on walls in a fire escape route will include fire-resistant additives. Paint in food preparation areas or nurseries will include antibacterial additives. A weather-resistant, fire-retardant, antibacterial paint would have multiple additives and multiple taggants corresponding to the selected additives.

A taggant or security marker is included in the paint. The taggant is added to the paint whilst the paint is in liquid form. The taggant can be introduced before or after the other components of the paint, or at the same time. In this embodiment, the taggant is combination of lanthanide-based ceramic taggants. The taggants together provide the paint with a signature emission spectrum which is difficult to fake. In one embodiment, a combination of $CeMgAl_{11}O_{19}:Tb^{3+}$, $BaMgAl_{10}O_{17}:Eu$ and $La_{0.60}Ce_{0.27}Tb_{0.13}PO_4$ is used. In a 1 kg sample of the paint, there will be about 1 g to 2.5 g of the taggant combination.

The paint can be applied to a substrate or surface like a wall or object in conventional manner. The time for the paint to dry fully depends on the carrier liquid or solvent, the ambient conditions, the other constituents of the paint, and the number of overall layers applied (and time between application of those layers). For example, for a layer 100 microns thick, suitable for fire-resistant paint, up to seven days may be needed before the paint has cured enough to be authenticated.

FIG. 1 illustrates a series of steps for authenticating the identity of the paint, once the paint has been applied to a surface and cured sufficiently. The surface in this embodiment is a non-metal surface. This assumes that the workman or workmen doing the painting are not being monitored by the authority responsible for authenticating the paint, for example.

A handheld reader is used to direct infra-red radiation onto the paint. The handheld reader can detect light across the IR and visible light range, to detect light which returns by reflection or emission from the paint. A return signal will be due to the presence of a taggant which absorbs the incident light and emits light in response. In other embodiments, the reader may direct UV light onto the paint.

If no light is detected, or the detected light can only be attributed to direct reflection, then the paint fails the authentication check because it is deemed not to include the taggant. The reader may have an LED (e.g. a red LED) which lights up to show this, or may issue a warning sound via a speaker, for example.

If a taggant is present, it will absorb the infra-red or UV light and either upconvert or downconvert the light, emitting a signature spectrum. This is detected by the reader and compared with a pre-programmed emission spectrum or set of emission spectra. The user may have the option to compare the reading to a particular spectrum, or the reader may automatically compare the reading to all of the programmed spectra.

If the emission spectrum from the paint matches closely enough (for example, within a 95% confidence interval) with the programmed data, then the paint passes the first stage of the authentication process. This may be sufficient in some cases where paint thickness is not at issue. For example, for antibacterial applications, paint thickness is of lesser importance compared to fire-related applications.

To check the paint thickness, the intensity of the matched emission spectrum is compared to the intensity of the detected light. A pre-programmed calibration curve is used to determine the thickness of the paint according to the intensity of detected light.

If the detected light intensity is too low, then there are too few layers of paint and the reader indicates that the paint has failed the check. Ideally the failure indication is different to the "no light emission" failure in the first step. In some cases, the shortfall in paint thickness may be indicated.

If the detected light intensity matches the expected value, or exceeds the required value, then the paint is deemed to pass the authentication check and the reader indicates the same with another LED or 'success' sound, for example.

In some embodiments, a camera is used to digitally record an image of the paint once irradiated with light which is expected to excite the taggant (with the expectation that a particular taggant is present to be excited). The image can be timestamped and/or tagged with location data. The image may be sent for off-site analysis, which streamlines the process of checking large buildings or estates which have many painted areas to authenticate.

It will be appreciated that the above description may applied in a similar way to a varnish.

In some embodiments, the paint or varnish may be conventional paint or varnish, and a separate taggant composition may be added to that paint or varnish at the point of use. This may be done by opening a tin or other container, optionally transferring the paint or varnish to a larger container, and adding a taggant composition (taggant, dispersant, additive(s)) to the paint or varnish. The composition is mixed in to ensure even dispersal of the taggant. The paint or varnish is then ready for use, and can be tested after paint or varnish application as above. It will be appreciated that the taggant composition may in some embodiments be added to the paint or varnish container and mixed in.

In another embodiment, a plastic body or item (or body/item made of a composite material) containing a taggant is provided. The plastic or composite material is manufactured or extruded into the body or item by conventional means. The taggant is added to the plastic or composite material prior to that manufacturing or extrusion step.

For example, the taggant may be added or incorporated into a starting material prior to manufacture or in the first step of manufacture. For example, a batch of plastic may be melted, taggant added and evenly dispersed, and the plastic then sent for processing into a particular form or shape.

The taggant composition may be mixed into plastic pellets for injection moulding, for example.

In similar embodiments, building elements such as carpet, floor tiles, linoleum or exterior cladding may be produced using plastic or composite materials containing the taggant or taggant composition. These building elements can be tested in a similar way to the paint/varnish discussed earlier.

In another embodiment, a method of sorting plastic items for recycling is provided. The plastic items contain a taggant or taggants according to the type of plastic incorporated in each item. For example, consider the following mixture of items:

- recyclable polythene bags, having a first taggant, or taggants in a signature ratio A;
- recyclable PET trays, having a second taggant, or taggants in a signature ratio B;
- recycled plastic containers, which cannot be recycled, having a third taggant, or taggants in a signature ratio C;
- non-recyclable plastics, having a fourth taggant, or taggants in a signature ratio D; and
- non-recyclable plastics having no taggant(s).

It will be appreciated that the exact form (tray etc.) and type of plastic (PET etc.) are not intended to be limiting here. The different forms and types are mentioned purely to exemplify the method. That is, to give examples of plastics and forms of plastic that are typically disposed of. Other plastics and forms of plastic item may be used in the method in other embodiments.

An automated or semi-automated system may be configured to sort the above mixture (or other mixtures containing plastic items) as follows. The items can be advanced, e.g. sequentially/one by one, through a light emitting and detecting system. The light emitter should be configured to emit IR or UV light at wavelengths which will stimulate emission from taggants in the plastics.

During use, where no emitted light is detected (non-recyclable plastic), the item is sent to waste, or for manual sorting. Where emitted light is detected, the light is compared to a record or database of known taggant emission wavelengths or spectra.

Once the plastic type is identified via this comparison, the plastic item can be sent to the correct destination for items of that particular plastic material or group of plastic materials. This facilitates more efficient recycling of plastics. It will be appreciated that this could equally be applied for sorting other synthetic materials.

In the above case, there are two sorts of plastic with taggant that may be grouped separately for recycling. These types of plastics may be and sorted sequentially, or may be sorted in parallel.

It will be appreciated that whilst the items may be scanned one by one, the items may be scanned in batches or in bulk. The system may physically or digitally tag/track the various items as they advance for sorting. Automated means such as a robotic arm or other device(s) capable of picking up a plastic item or isolating a plastic item from other items may then sort or segregate selected plastic items to form a batch suitable for recycling.

In other embodiments, the plastic items to be sorted may include one type of plastic with taggant, and a second type of plastic without taggant. The mixed plastics can be sorted into batches of similar or same plastics for recycling in an analogous way.

It will be appreciated that the system may also be adapted to sort plastic from mixed waste or mixed materials in a more general sense. For example, the process may be used to separate plastic from waste or rubbish in a landfill site for example, or from rubbish which is destined for landfill.

That is, the waste stream or stream of recycled materials may include non-plastics such as any one or more of: metal, glass, wood, paper and/or other non-plastic materials. The sorting process may therefore be used to generally sort taggant-containing materials into one or more groups of similar taggant-containing materials, and at least one group of non-taggant-containing materials.

The invention is therefore substantially useful in multiple ways. In any embodiment, taggant(s) may be added/included at the manufacturing stage of a paint or varnish, or a plastic or composite material (or product containing such). This enables independent authentication of the product identity after application and/or for recycling purposes, according to the product containing the taggant.

The embodiments described above are provided by way of example only, and various changes and modifications will be apparent to persons skilled in the art without departing from the scope of the present invention as defined by the appended claims.

The invention claimed is:

1. A paint or varnish comprising:
   in respect of paint, a pigment;
   a carrier liquid;
   a binder;
   one or more additives; and
   one or more inorganic or ceramic taggants selected to correspond to the one or more additives,
   wherein the one or more taggants are provided in an amount up to 0.1% by weight of the paint or varnish, the one or more taggants are evenly dispersed and suspended in the carrier liquid, and the one or more taggants have a particle size or particle size range suitable for remaining in suspension, and
   wherein for authentication of the paint or varnish on a substrate the one or more taggants are excitable by infra-red or ultraviolet light at one wavelength to emit light at one or more other wavelengths, the emission wavelength or spectrum of the one or more taggants being indicative of the one or more additive in the paint or varnish for use in authenticating the paint or varnish.

2. A paint or varnish as claimed in claim 1, in which there is a plurality of inorganic or ceramic taggants in a signature ratio, providing a signature emission spectrum for authenticating the paint or varnish.

3. A paint or varnish as claimed in claim 2, in which the plurality of inorganic or ceramic taggants includes a plurality of lanthanide elements to provide the signature emission spectrum.

4. A paint or varnish as claimed in claim 1, in which the one or more additive include one or more of the following:
   one or more fire-resistant components;
   one or more antibacterial components;
   one or more antiviral components;
   one or more antifungal components;
   one or more non-slip components or compounds; and
   one or more anti-slip components or compounds.

5. A paint or varnish as claimed in claim 4, comprising one or both of the following:
   where the one or more fire-resistant components are provided, the one or more taggants emit red or reddish light following infra-red or ultraviolet excitation for indicating said components are present; and
   where any of the one or more antibacterial components, the one or more antiviral components and the one or more antifungal components are provided, the one or more taggants green or greenish light following infrared or ultraviolet excitation for indicating said components are present.

6. A paint or varnish as claimed in claim 4, in which the one or more antibacterial components include silver ions.

7. A method of non-destructively authenticating the identity of a paint or varnish on a substrate, comprising the steps of:
   a) directing ultraviolet or infrared light onto the paint or varnish for exciting one or more inorganic or ceramic taggants if present in the paint or varnish;
   b) detecting light, if any, which is subsequently emitted from the paint or varnish after ultraviolet or infrared light absorption; and
   c) comparing the detected light to an expected signature emission wavelength or spectrum of the paint or varnish, to determine whether the correct paint or varnish according to claim 1 has been applied and, if so, optionally whether the paint or varnish has been applied to the substrate at a suitable thickness.

8. A method as claimed in claim 7, in which the substrate is a non-metal substrate.

9. A method as claimed in claim 7, in which step (c) includes comparing the intensity of the detected light to an expected intensity value or range for assessing the thickness of the paint or varnish on the substrate.

10. A method as claimed in claim 7, in which steps (a) to (c) are performed using a hand-held device held against or near the paint or varnish on the substrate, the hand-held device including one or more of:
    an infra-red emitter for directing light onto the paint or varnish in step (a);
    an ultraviolet emitter for directing light onto the paint or varnish in step (a); and
    a sensor capable of detecting one or more of: ultraviolet light, visible light and infra-red light.

11. A method as claimed in claim 10, in which the hand-held device is programmed with a plurality of signature emission wavelengths and/or spectra, for authenticating a plurality of different paints or varnishes.

12. A method as claimed in claim 7, including recording an image of the paint or varnish during or immediately following excitation, for authenticating the paint or varnish off-site, further comprising neither of, one of or both of the following steps:
    a timestamp is applied to or associated with the recorded image; and
    location data is applied to or associated with the recorded image.

13. A taggant composition for addition to a paint or varnish, the taggant composition comprising one or more inorganic or ceramic taggants, one or more additives, and a dispersant, the one or more taggants corresponding to the one or more additives, the one or more taggants being evenly dispersed and suspended in the dispersant, the one or more taggants having a particle size or particle size range suitable for remaining in suspension, in which for authentication of the taggant composition in a paint or varnish on a substrate the one or more taggants are excitable by infra-red or ultraviolet light at one wavelength to emit light at one or more other wavelengths, the emission wavelength or spectrum of the one or more taggants being indicative of the additive(s) in the taggant composition for use in authenticating the taggant composition as part of a paint or varnish.

14. A taggant composition as claimed in claim 13, in which there is a plurality of inorganic or ceramic taggants in a signature ratio, providing a signature emission spectrum for authenticating the paint or varnish.

15. A taggant composition as claimed in claim 14, in which the plurality of inorganic or ceramic taggants includes a plurality of lanthanide elements to provide the signature emission spectrum.

16. A taggant composition as claimed in claim 13, in which the one or more additive include one or more of the following:
    one or more fire-resistant components;
    one or more antibacterial components;
    one or more antiviral components;
    one or more antifungal components;
    one or more non-slip components or compounds; and
    one or more anti-slip components or compounds.

17. A taggant composition as claimed in claim 16, in which comprising one or both of the following:
    where the one or more fire-resistant components are provided, the one or more taggants emit red or reddish light following infra-red or ultraviolet excitation for indicating said components are present; and
    where any of the one or more antibacterial components, the one or more antiviral components and the one or more antifungal components are provided the one or more taggants emit green or greenish light following infra-red or ultraviolet excitation for indicating said components are present.

18. A taggant composition as claimed in 16, in which the one or more antibacterial components include silver ions.

19. A method of manufacturing or modifying a paint or varnish, the method including the steps of:
    a) providing a paint comprising a pigment, a carrier liquid, and a binder; or providing a varnish;
    b) providing a taggant composition as claimed in claim 13, in which the one or more taggants in the taggant composition are provided in an amount up to 0.1% by weight of the paint or varnish; and
    c) mixing the taggant composition into the paint or varnish such that the one or more taggants becomes evenly dispersed and suspended in the paint or varnish, the one or more taggants having a particle size or particle size range suitable for remaining in suspension.

20. A method as claimed in claim 19, in which the paint or varnish is provided in a first container, and the taggant composition is provided in a second container which is smaller than the first container.

* * * * *